United States Patent

Santiesteban et al.

[11] Patent Number: 5,491,273
[45] Date of Patent: Feb. 13, 1996

[54] CATALYTIC CONVERSION OF METHANOL TO LINEAR OLEFINS

[75] Inventors: Jose G. Santiesteban, Yardley, Pa.; Clarence D. Chang, Princeton, N.J.; James C. Vartuli, West Chester, Pa.; David H. Olson, Pennington, N.J.

[73] Assignee: Mobil Oil Corporation, Fairfax, Va.

[21] Appl. No.: 340,787

[22] Filed: Nov. 17, 1994

[51] Int. Cl.$^6$ ............................................. C07C 1/00
[52] U.S. Cl. ............................................. 585/639
[58] Field of Search ............................................. 585/639

[56]  References Cited

U.S. PATENT DOCUMENTS

| | | | |
|---|---|---|---|
| 3,894,106 | 7/1975 | Chang et al. | 260/668 R |
| 3,979,472 | 9/1976 | Butter | 260/668 R |
| 3,998,898 | 12/1976 | Chang et al. | 260/668 R |
| 4,025,571 | 5/1977 | Lago | 260/668 D |
| 4,025,572 | 5/1977 | Lago | 260/668 D |
| 4,025,575 | 5/1977 | Chang et al. | 260/682 |
| 4,148,835 | 4/1979 | Chen et al. | 260/682 |

*Primary Examiner*—E. Rollins Cross
*Assistant Examiner*—E. D. Irzinski
*Attorney, Agent, or Firm*—Alexander J. McKillop; Malcolm D. Keen; Richard D. Stone

[57] ABSTRACT

This invention covers a process for converting a feed comprising at least one lower aliphatic alcohol having from 1 to 3 carbon atoms or a corresponding ether of such an alcohol to hydrocarbon products comprising linear olefins. The process comprises contacting the feed in a reaction zone with a catalyst comprising material having a large crystal ferrierite aluminosilicate structure. An effluent is withdrawn from the reaction zone, which comprises linear olefins. Linear olefins may then be separated from the effluent. The aliphatic alcohol having from 1 to 3 carbons is generally methanol and the preferred ether is dimethyl ether. ZSM-35 is the preferred large crystal ferrierite structure of this invention.

9 Claims, No Drawings

CATALYTIC CONVERSION OF METHANOL TO LINEAR OLEFINS

FIELD OF THE INVENTION

The instant invention relates to the production of olefins, particularly linear olefins, from a feed comprising at least one lower aliphatic alcohol such as methanol or its corresponding ether such as dimethyl ether. Linear olefins are important compounds for the efficient coproduction of clean fuels, lubes and petrochemicals. The alcohol may be mixed with a diluent, such as nitrogen, or other hydrocarbons. More particularly, the invention relates to the catalytic conversion of the feed to an olefinic product using catalysts comprising material having large crystal ferrierite aluminosilicate zeolite structures.

BACKGROUND OF THE INVENTION

The demand for olefinic feedstocks has increased rapidly in the past few years due to the increased need for synthetic fibers, plastics and petrochemicals. The increase in demand for olefinic feedstocks, such as ethylene and propylene, n-butylene and n-pentene has periodically caused a shortage of these basic raw materials either because of a limitation in petroleum feedstock of suitable quality or a limitation in the present olefinic production capacity. Thus, alternative sources of ethylene production from non-petroleum sources are required to keep pace with the demand for ethylene and other olefins.

It is now known that feed comprising lower alcohols and/or oxygenates thereof, such as methanol, ethanol, ether, (e.g., dimethyl ether), aldehydes and ketones, can be converted to gasoline grade hydrocarbons or to olefins by contacting the feed with zeolite catalysts.

U.S. Pat. No. 3,894,106 is directed to the production of olefins from aliphatic ethers by catalytic conversion with, for example, an HZSM-5 zeolite catalyst.

U.S. Pat. No. 3,979,472 is directed to the conversion of lower alcohols and their ethers with a composite of antimony oxide and a ZSM-5 zeolite to produce a mixture of ethylene, propylene and mononuclear aromatics.

U.S. Pat. No. 4,025,572 improved the processes for ethylene selectivity by diluting a ZSM-5 zeolite with an inert diluent. A similar result is achieved through the use of subatmospheric partial pressure of the feed, according to U.S. Pat. No. 4,025,575.

U.S. Pat. No. 4,025,571 is directed to processes for improved ethylene selectivity by employing a ZSM-5 zeolite in a large crystal form of at least about 1 micron.

U.S. Pat. No. 4,148,835 discloses the combination of the large crystal ZSM-5 zeolite and added metals.

Olefin production from feeds comprising aliphatic alcohols or both may be conducted in a fixed bed in a fixed bed tubular reactor, moving bed reactor or in a fluidized bed reactor. If the process, known as methanol-to-gasoline (MTG) or methanol-to-chemicals (MTC) process depending upon the product obtained, is conducted in a fixed bed or a fixed bed tubular reactor, it is usually carried out in two stages. The first stage comprises the conversion of the feed to dimethyl ether (DME) in the DME reactor, and the second stage the conversion of the effluent of the DME reactor to the gasoline boiling point range hydrocarbons or to chemicals, such as olefins. Both stages of the reaction are carried out in the presence of a catalyst: the first stage with a gamma alumina catalyst (see, e.g., U.S. Pat. No. 3,931,349), and the second stage with an intermediate pore zeolite catalyst, such as, for example, ZSM-5. If the reaction is carried out in a fluidized bed reactor, the entire course of the reaction is catalyzed by an intermediate pore zeolite catalyst (see, e.g., U.S. Pat. No. 3,998,898). The intermediate pore zeolite catalysts used in the process are characterized by a silica ($SiO_2$) to alumina ($Al_2O_3$) mole ratio of at least 12, a Constraint index of about 1 to 12 and a crystal density of at least 1.6 grams per cubic centimeter ($g/cm^3$).

SUMMARY OF THE INVENTION

Technologies for production and conversion of olefins are important for the efficient coproduction of clean fuels, lubes, and petrochemicals. In accordance with the instant invention, it has been found that in the catalytic conversion of alcohols to olefins, such as n-butene or n-pentene, the proportion of linear olefinic hydrocarbons in the product stream can be desirably and dramatically increased by contacting the vaporous alcohol with a large crystal ferrierite aluminosilicate catalyst. Such a catalyst has an average crystal size larger than 0.2 microns.

It is expected that the selectivity to other, higher olefins, with five or more carbon atoms, can be improved by selectively reducing or eliminating the external active sites of the large crystal ferrierite aluminosilicate catalyst. This is done by coke selectivation, treatment with oxalic acid, inorganic oxides, steaming, etc.

The conversion of alcohols to hydrocarbons is carried out by passing a feed comprising one or more compounds selected from the group consisting of lower monohydric alcohols with up to 4 carbon atoms and their simple and fixed ether derivatives over a catalyst contained in a reaction zone. An effluent comprising a mixture of light olefins, paraffin hydrocarbons and aromatic hydrocarbons is withdrawn from the reaction zone. The light olefins are then segregated from the effluent.

DETAILED DESCRIPTION OF THE INVENTION

The present invention relates to improvements in the catalytic conversion of methanol, its corresponding ether, i.e. DME, or mixtures thereof, to olefinic hydrocarbons. Methanol is preferred and may be substantially pure, industrial grade anhydrous methanol or even crude methanol containing usually 12 to 20 wt. % of water. Diluents may be included in the alcohol feed. Diluents include, but are not limited to: steam, hydrogen, helium, nitrogen, carbon dioxide, methane, ethane, propane, butane, pentane, hexane, heptane and flue gas.

Catalysts useful in this invention comprise large crystal, ferrierite aluminosilicate zeolite structures such as ZSM-35. Other aluminosilicates, natural or synthetic, having an equivalent structure can also be suitable catalysts for the reactions of this invention. ZSM-35 is a multi-channel zeolite. Depending on the morphology of the crystals involved, such a zeolite may exhibit selectivities consistent with one channel over those of another channel. ZSM-35 possesses unequally sized channels, one exhibiting 8-membered ring characteristics and the other demonstrating 10-member ring characteristics. As the crystal size increases the 8-member ring characteristics dominate.

ZSM-35 is more particularly described in U.S. Pat. No. 4,016,245, the entire contents of which are incorporated herein by reference. Isotypes of ZSM-35 include ferrierite (P. A. Vaughan, Acta Cryst, 21, 983 (983 (1966); FU-9 (D. Seddon and T. V. Whittam, European Patent B-55,529, 1985); ISI-6 (N. Morimoto, K. Takatsu and M. Sugimoto, U.S. Pat. No. 4,578,259, 1986); monoclinic ferrierite (R. Gramlich-Meier, V. Gramlich and W. M. Meier, Am. Mineral. 70,619 (1985)); NU-23 (T. V. Whitman, European Patent A-103,981, 1984); and Sr-D (R. M. Barrer and D. J. Marshall, J. Chem. Soc. 1964, 2296 (1964)). An example of a piperidine-derived ferrierite is more particularly described in U.S. Pat. No. 4,343,692, the entire contents of which are incorporated herein by reference. Other synthetic ferrierite preparations are described in U.S. Pat. Nos. 3,933,974; 3,966,883; 4,000,248; 4,017,590; and 4,251,499, the entire contents of all being incorporated herein by reference. Further description of ferrierite are found in Kibby et al., "Composition and Catalytic Properties of Synthetic Ferrierite," Journal of Catalysis, 35, pages 256–272 (1974).

In the preparation of large crystal ZSM-35 the synthesis temperature is a key factor. Higher temperatures, such as 347° F. (175° C.) favor large crystal formation (see Example 1). Lower temperatures, such as 221° F. (105° C.) favor the development of small crystals (see Example 3).

The catalysts useful in this invention possess an average crystal size larger than 0.2 microns, preferably larger than 0.5 microns, and more preferably larger than 1.0 microns. The constraint index(CI) for ZSM-35 is about 4.5. The method by which Constraint Index is determined is described fully in U.S. Pat. No. 4,016,218, to which reference is made for details of the method.

Natural zeolites may sometimes be converted to zeolite structures of the class herein identified by various activation procedures and other treatments, such as base exchange, steaming, alumina extraction and calcination, alone or in combination. Natural minerals which may be so treated include ferrierite, brewsterite, stilbite, dachiardite, epistilbite, hepulandite, and clinoptilolite.

The zeolite of the present invention may include a hydrogenation-dehydrogenation component (referred to, for convenience, as a hydrogenation component) which is generally a metal or metals of groups IB, IIB, VA, VIA or VIIIA of the Periodic Table (IUPAC and U.S. National Bureau of Standards approved Table, as shown, for example, in the Chart of the Fisher Scientific Company, Catalog No. 5-702-10). The preferred hydrogenation components are the noble metals, such as palladium, gold, silver, rhenium or rhodium, may also be used. Combinations of noble metals, such as platinum-rhenium, platinum-palladium, platinum-iridium or platinum-iridium-rhenium, together with combinations of non-noble metals, particularly of Groups VIA and VIIA, are of interest, particularly with metals such as cobalt, nickel, vanadium, tungsten, titanium and molybdenum, for example, platinum-tungsten, platinum-nickel or platinum-nickel-tungsten. Base metal hydrogenation components may also be used, especially nickel, cobalt, molybdenum, tungsten, copper or zinc. Combinations of base metals, such as cobalt-nickel, cobalt-molybdenum, nickel-tungsten, cobalt-nickel-tungsten or cobalt-nickel-titanium, may also be used.

The metal may be incorporated into the catalyst by any suitable method, such as impregnation or exchange, onto the zeolite. The metal may be incorporated in the form of a cationic, anionic or a neutral complex, such as $Pt(NH_3)_4^{2+}$, and cationic complexes of this type will be found convenient for exchanging metals onto the zeolite. Anionic complexes are also useful for impregnating metals into the zeolites.

The amount of the hydrogenation-dehydrogenation component is suitably from 0.01 to 25% by weight, normally 0.1 to 5% by weight, especially for noble metals, and preferably 0.3 to 1% by weight, although this will, of course, vary with the nature of the component. For example, less of the highly active noble metals, particularly platinum, is required than of the less active metals.

The original cations associated with each of the crystalline silicate zeolites utilized herein may be replaced by a wide variety of other cations according to techniques well known in the art. Typical replacing cations include hydrogen, ammonium, alkyl ammonium and metal cations, including mixtures of the same. Of the replacing metallic cations, particular reference is given to cations of metals, such as the rear earth metals of manganese, as well as metals of Groups IIA and B of the Periodic Table, e.g., zinc, and Group VIII of the Periodic Table, e.g., nickel, platinum and palladium.

Typical ion exchange techniques are to contact the particular zeolite with a salt of the desired replacing cation. Although a wide variety of salts can be employed, particular preference is given to chlorides, nitrates and sulfates. Representative ion exchange techniques are disclosed in a wide variety of patents, including U.S. Pat. Nos. 3,140,249; 3,140,249; 3,140,251; and 3,140,253.

Alternatively, the metallic catalyst component can be incorporated into the zeolite by impregnating the zeolite with a solution of the metal or metal compounds or complexes, followed by stripping of the solvent employed. Metallic compound incorporation can also be accomplished by sorbing metal compounds or complexes into the zeolite. Thus, such materials as nickel carbonyl or rhodium carbonyl chloride can be sorbed from solution or from the gas phase into the zeolite structure.

Following contact with a solution of the desired replacing cation, the zeolite is then preferably washed with water and dried at a temperature ranging from 150° F. (70° C.) to about 600° F. (320° C.) and thereafter calcined in air, or other inert gas at temperatures ranging from about 500° F. (230° C.) to 1500° F. (820° C.) for periods of time ranging from 1 to about 48 hours or more. It has been further found that catalysts of improved selectivity and other beneficial properties may be obtained by subjecting the zeolite to treatment with steam at elevated temperatures ranging from 500° F. (230° C.) to 1200° F. (650° C.), and preferable 750° F. (400° C.) to 1000° F. (540° C.). The treatment may be accomplished in an atmosphere of 100% steam or an atmosphere consisting of team and a gas which is substantially inert to the zeolites. A similar treatment can be accomplished at lower temperatures and elevated pressure, e.g., 350°–700° F. (180°–370° C.) at 10 to about 200 atmospheres.

In practicing a particularly desired chemical conversion process, it may be useful to incorporate the above-described crystalline zeolite with a matrix comprising another material resistant to the temperature and other another material resistant to the temperature and other conditions employed in the process. Such material is useful as a binder and imparts greater resistance to the catalyst for the severe temperature, pressure and reactant feed stream velocity conditions encountered in many cracking processes.

Useful matrix materials include both synthetic and naturally occurring substances, as well inorganic materials, such as clay, silica and/or metal oxides. The latter may be either naturally occurring or in the form of gelatinous precipitates or gels, including mixtures of silica and metal oxides. Naturally occurring clays which can be composited with the zeolite include those of the montmorillonite and kaolin families, which families include the sub-bentonites and the kaolin families, which families include the sub-bentonites and the kaolins commonly known as Dixie, McNamee-Georgia and Florida clays, or others in which the main mineral constituent is halloysite, kaolinite, dickite, nacrite or anauxite. Such clays can be used in the raw state, as originally mined or initially subjected to calcination, acid treatment or chemical modification.

The conversion process described herein may be carried out as a batch-type, semi-continuous or continuous operation utilizing a fixed or moving bed reactor conducted to a regeneration zone, wherein coke is burned from the catalyst in an oxygen-containing atmosphere, e.g., air, at an elevated temperature, after which the regenerated catalyst is recycled to the conversion zone for further contact with the chargestock. The fixed bed reactor may be used in either upflow or downflow mode. Regeneration is carried out in a conventional manner, where an inert gas containing a small amount of oxygen (0.5–2%) is used to burn the coke in a controlled manner so as to limit the temperature to a maximum of around 300°–500° C.

For purposes of the present invention, the preferred alcohol feed is methanol and subsequent discussion of the conversion process will be with reference to the methanol feedstock. However, it is to be understood that such reference is intended to be for purposes of illustrating the invention and should not be taken as limiting the novel process disclosed herein.

The methanol feed is passed over the catalyst at a rate of 0.5–10 WHSV (weight hourly space velocity), preferably at 1–5 WHSV. In all cases, the WHSV is calculated on the pounds of methanol feed per hour per pound of catalyst. Because it is well known that high operating pressures result in reduced yields of light olefins, the inlet pressure to the reactor should be less than 100 psig, preferably less than 40 psig, and most preferably about 25 psig. The total system pressure may range from 1 to 100 atmospheres, preferably from 1 to 40 atmospheres. The conversion is carried out at temperatures between about 480° F. (250° C.) and 1112° F. (600° C.) with the preferred operating temperature range being between 530° F. (275° C.) and 930° F. (500° C.) It is understood that the temperatures referred to herein are the maximum temperature within the reaction zone. Thus, in a fixed bed operations, the inlet temperature may be lower than 480° F. (250° C.).

Within the prescribed conditions, a conversion per pass of from 5% to about 90% of the methanol feed may be achieved and the ratio of $C_2$–$C_4$ olefins to paraffins in the product mix is significantly enhanced The term "conversion" as used herein, is to be understood to mean a chemical change in which a hydrocarbon having at least 2 carbon atoms is formed. Thus, a substantially pure methanol feed will initially form an equilibrium mixture of alcohol, DME and water, which is then further converted to a mixture of hydrocarbons and water. This DME is ignored in computing conversion, since no new carbon-carbon bonds are created in its formation. If some DME is present in the methanol feed, its conversion to hydrocarbons is added to that of the methanol to arrive at the "conversion" value. Specifically, 80% conversion as used herein means that 80% of the total-$CH_2$-groups present in the methanol and DME of the methanol feed are converted to hydrocarbons.

The hydrocarbon mixture produced by the process of this invention is recovered and the linear olefins concentrated and separated by distillation or other techniques well understood in the refining arts.

The following examples will serve to illustrate the process of the invention but are not to be considered limiting.

EXAMPLES

The conversion of methanol to linear olefins was performed in a fixed-bed flow reactor. The feed consisting of methanol and nitrogen was passed at 1 atmosphere pressure over the catalyst. Reactor effluent was analyzed by on-line gas chromatography. Water was not analyzed, so product distribution is on water-fee basis. Temperatures, methanol partial pressures, and flow rates, expressed as WHSV=g methanol per g zeolite per hour, are indicted in the tables along with the product distribution.

EXAMPLE 1

This example illustrates the preparation of large crystal ZSM-35.

Water (143 grams), sodium hydroxide (50 wt %), 9.6 grams, aluminum sulfate (9.1 grams), HiSil 233 (16.1 grams), and pyrollidine (22.1 grams) were combined in order with mixing. The mixture was placed in a stirred autoclave and crystallized at 175° C. for 24 hours with stirring. A high temperature, as used in this example, is conducive to the preparation of large crystal ZSM-35. The zeolite was recovered by filtration and washing. It was then calcined in $N_2$ at 540° C. to decompose the organic solvent, exchanged with 1N $NH_3NO_3$ solution to remove the sodium, and finally calcined in air to remove the organic solvent. The approximate crystal size as determined by Scanning Electron Microscopy (SEM) was 1–3 microns.

EXAMPLE 2

Large crystal ZSM-35 prepared according to Example 1 was steamed at 593° C. for 48 hours and then refluxed for 24 hours with 1N ammonium nitrate, with subsequent calcination in flowing nitrogen at 538° C. until all the ammonia was removed. The approximate crystal size as determined by Scanning Electron Microscopy (SEM) was 1–3 microns.

EXAMPLE 3

This example illustrates the preparation of small crystal ZSM-35. the temperature used in this example is somewhat lower than that used in Example 1. This lower temperature is conducive to the preparation of small crystal ZSM-35.

9.42 parts distilled $H_2O$ were charged to an autoclave, followed by 1.38 parts of NaOH solution (50% by wt) and 1.18 part of aluminum sulfate (71.2% $Al_2O_3$). 0.03 parts of ZSM-35 seeds (100% basis) and 3.20 parts of HiSil 233 precipitated silica were added with stirring, followed by 1.0 part of pyrrolidine. The autoclave was heated to 105° C. with stirring and the gel crystallized for 74 hours. After flashing the pyrrolidine, the ZSM-35 product was filtered, washed with deionized water, and dried at 120° C. The ZSM-35 zeolite was steamed at 593° C. for 48 hours and then refluxed 24 hours with 1N ammonia nitrate and calcined in flowing nitrogen at 538° C. until all the ammonia was removed. The approximate crystal size, as determined by Scanning Electron Mircographs (SEM) and Transmission Electron Micrographs was 0.05 microns.

EXAMPLES 4–8

Example 4 described the results obtained on the conversion of methanol over large crystal ZSM-35 catalyst prepared according to Example 1. Examples 5 to 8 present the results obtained over large crystal ZSM-35 prepared according to Example 2. The results are presented in Table 1 along with the operating conditions.

TABLE 1

| | Example: | | | | |
|---|---|---|---|---|---|
| | 4 | 5 | 6 | 7 | 8 |
| Methanol Partial Pressure (atm) | 1 | 0.13 | 0.13 | 0.13 | 0.13 |
| Temperatures (°C.) | 400 | 400 | 400 | 400 | 400 |
| WHSV | 1.6 | 2.0 | 2.0 | 4.1 | 9.9 |
| Methanol Conversion | 100 | 95.1 | 83.2 | 77.9 | 73.3 |
| Hydrocarbon Product Distribution (wt %) | | | | | |
| Methane | 5.3 | 1.9 | 3.1 | 1.8 | 25.7 |
| Ethane | 1.7 | 0.3 | 0.3 | 0.3 | 1.3 |
| Ethylene | 10.2 | 6.4 | 5.6 | 6.9 | 8.3 |
| Propane | 3.2 | 2.2 | 1.7 | 1.8 | 1.0 |
| Propylene | 12.9 | 8.7 | 8.4 | 10.2 | 10.2 |
| Isobutane | — | 0.4 | 0.2 | 0.3 | 0.2 |
| n-Butane | 2.0 | 2.0 | 1.6 | 1.8 | 1.2 |
| Isopentane | — | 0.7 | — | — | — |
| n-Pentane | 1.6 | 1.5 | 1.2 | 1.4 | — |
| n-Butene | 30.2 | 15.4 | 18.7 | 22.9 | 23.6 |
| Isobutene | 2.7 | 4.7 | 4.2 | 2.0 | 0.7 |
| n-Pentene | 7.3 | 13.7 | 16.0 | 18.0 | 14.5 |
| Isopentene | 19.4 | 34.1 | 29.1 | 25.2 | 12.4 |
| $C_6^{30}$ (mainly $C_6=$) | 3.2 | 7.8 | 9.7 | 7.1 | 1.0 |

EXAMPLES 9–10

These examples show the results obtained on the conversion of methanol over the catalyst prepared in Example 3, small crystal ZSM-35. The results are presented in Table 2 along with the operating conditions.

Table 3 summarizes the $C_4$ olefin distribution obtained over catalysts of Example 1, large crystal ZSM-35, and Example 3, small crystal ZSM-35. The $C_4$ paraffin distribution, which reflects the $C_4$ olefin selectivity, is also given for the sake of comparison. These data clearly show that the large crystal ZSM-35 catalyst is significantly more selective for the production of linear butenes.

TABLE 2

| | Example: | |
|---|---|---|
| | 9 | 10 |
| Methanol Partial Pressure (atm) | 0.13 | 0.13 |
| Temperature (°C.) | 400 | 400 |
| WHSV | 0.5 | 0.5 |
| Methanol conversion | 90.5 | 65.0 |
| Time on Stream, hours,. | 0.03 | 0.1 |
| Hydrocarbon Product Distribution wt %) | 90.5 | 65.0 |
| Methane | 3.5 | 11.2 |
| Ethane | 0.1 | 0.2 |
| Ethylene | 5.1 | 5.7 |
| Propane | 1.1 | 0.8 |
| Propylene | 5.0 | 4.1 |
| Isobutane | 1.2 | 0.8 |
| n-Butane | 1.3 | 0.9 |
| Isopentane | 2.9 | 1.5 |
| n-Pentane | 1.0 | 0 |
| n-Butene | 10.5 | 11.8 |
| Isobutene | 7.0 | 6.0 |
| n-Pentene | 11.1 | 11.8 |
| Isopentene | 29.5 | 29.2 |
| $C_6^+$ (mainly $C_6=$) | 20.4 | 16.0 |

TABLE 3

| | Temp. (C.°) | Methanol Conv. (%) | $C_4$ Olefin Dist. (%) | | n-Butene: Isobutylene | $C_4$ Paraffin Dist. (%) | |
|---|---|---|---|---|---|---|---|
| | | | n-Butenes | Isobutylene | | n-Butane | Isobutane |
| Large Crystal ZSM-35 | 400 | 95.1 | 76.6 | 23.4 | 3.3 | 83.3 | 16.7 |
| | 400 | 77.9 | 92.0 | 8.0 | 11.5 | 85.7 | 14.3 |
| | 500 | 73.3 | 97.1 | 2.9 | 33.5 | 85.7 | 14.3 |
| Small Crystal ZSM-35 | 400 | 90.5 | 60.0 | 40.0 | 1.33 | 52.0 | 48.0 |
| | 400 | 64.4 | 66.3 | 33.7 | 1.85 | 53.0 | 47.0 |

We claim:

1. A process for converting a feed comprising at least one lower aliphatic alcohol having from 1 to 3 carbon atoms or a corresponding ether of such an alcohol to hydrocarbon products comprising linear olefins, the process comprising contacting the feed in a reaction zone with a catalyst comprising material having a large crystal ferrierite aluminosilicate structure, the aluminosilicate catalyst comprising a hydrogenation component, the hydrogenation component comprising combinations of Group VIA and VIIIA metals, wherein the average crystal size is larger than 0.5 microns and is selected from the group consisting of ZSM-35,FU-9,ISI-6,NU-23and SR-D, withdrawing from the reaction zone an effluent comprising linear olefins, and separating the linear olefins from the effluent.

2. The process of claim 1, wherein the aliphatic alcohol having from 1 to 3 carbons is methanol and the ether is dimethyl ether.

3. The process of claim 1, wherein the feed further comprises diluents.

4. The process of claim 3, wherein the diluents are selected from the group consisting of steam, hydrogen, helium, nitrogen, carbon dioxide, methane, ethane, propane, butane, hexane, heptane and flue gas.

5. The process of claim 1, wherein the material is ZSM-35.

6. The process of claim 1, wherein the average crystal size is larger than 1.0 microns.

7. The process of claim 1, wherein the reaction zone is a fixed-bed flow reactor.

8. The process of claim 1, wherein conversion of the feed occurs at a temperature in the range from about 480° F. to 1112° F.

9. The process of claim 1, wherein conversion of the feed occurs at a total system pressure of from about 1 to 100 atmospheres.

* * * * *

UNITED STATES PATENT AND TRADEMARK OFFICE
CERTIFICATE OF CORRECTION

PATENT NO. : 5,491,273
DATED : February 13, 1996
INVENTOR(S) : Clarence D. Chang, et. al.

It is certified that error appears in the above-indentified patent and that said Letters Patent is hereby corrected as shown below:

Columns 7-8-  Table 2 should all be printed in Column 8--.

Signed and Sealed this

Thirtieth Day of July, 1996

Attest:

BRUCE LEHMAN

Attesting Officer

Commissioner of Patents and Trademarks